United States Patent
Ruiz

(10) Patent No.: US 10,492,840 B2
(45) Date of Patent: *Dec. 3, 2019

(54) DISTRACTOR DEVICE INCLUDING MULTIPLE DIAMETER INTERNAL POST AND RELATED METHODS

(71) Applicant: Ramon L. Ruiz, Winter Park, FL (US)

(72) Inventor: Ramon L. Ruiz, Winter Park, FL (US)

( * ) Notice: Subject to any disclaimer, the term of this patent is extended or adjusted under 35 U.S.C. 154(b) by 800 days.

This patent is subject to a terminal disclaimer.

(21) Appl. No.: 15/094,136

(22) Filed: Apr. 8, 2016

(65) Prior Publication Data

US 2016/0220287 A1  Aug. 4, 2016

Related U.S. Application Data

(63) Continuation of application No. 13/984,333, filed as application No. PCT/US2012/034161 on Apr. 19, 2012, now Pat. No. 9,308,026.

(Continued)

(51) Int. Cl.
*A61B 17/66* (2006.01)
*A61B 17/80* (2006.01)
(Continued)

(52) U.S. Cl.
CPC ........ *A61B 17/8019* (2013.01); *A61B 17/663* (2013.01); *A61B 17/8071* (2013.01);
(Continued)

(58) Field of Classification Search
CPC .............. A61B 17/8019; A61B 17/663; A61B 17/8071; A61B 17/6425; A61B 17/6433; A61B 17/645; A61B 17/6458; A61B 17/6466; A61B 17/6475; A61B 17/6483; A61B 17/6491; A61B 17/66; A61B 17/666; A61B 2017/681; A61B 2017/00402

See application file for complete search history.

(56) References Cited

U.S. PATENT DOCUMENTS 4,621,627 A * 11/1986 DeBastiani ............ A61B 17/66
606/57
4,978,347 A    12/1990 Ilizarov
(Continued)

FOREIGN PATENT DOCUMENTS

DE  29716635  10/1997
DE  20008797  8/2000

*Primary Examiner* — Zade Coley
(74) *Attorney, Agent, or Firm* — Allen, Dyer, Doppelt + Gilchrist, P.A.

(57) ABSTRACT

A distractor device may include a tubular body being internally threaded, a first foot plate extending from the tubular body, and an internal post in the tubular body. The internal post may include a first portion having a first diameter being externally threaded to cooperate with the internally threaded tubular body, and a second portion coupled to the first portion, having a second diameter less than the first diameter, and also being externally threaded. The tubular body may include a longitudinal slot extending from adjacent the first foot plate. The distractor device may include a second foot plate extending through the longitudinal slot and for threadingly coupling to the externally threaded second portion of the internal post. The second portion may include a tool interface on a distal end thereof.

21 Claims, 5 Drawing Sheets

Related U.S. Application Data

(60) Provisional application No. 61/477,253, filed on Apr. 20, 2011.

(51) Int. Cl.
*A61B 17/00* (2006.01)
*A61B 17/68* (2006.01)

(52) U.S. Cl.
CPC ............ *A61B 2017/00398* (2013.01); *A61B 2017/00402* (2013.01); *A61B 2017/681* (2013.01); *Y10T 29/49826* (2015.01)

(56) References Cited

U.S. PATENT DOCUMENTS

| | | | |
|---|---|---|---|
| 5,067,954 A | 11/1991 | Ilizarov | |
| 5,160,335 A * | 11/1992 | Wagenknecht | A61B 17/6466 606/57 |
| RE34,985 E * | 6/1995 | Pennig | A61B 17/6416 606/57 |
| 5,540,687 A * | 7/1996 | Fairley | A61B 17/66 606/105 |
| 6,113,599 A * | 9/2000 | Landsberger | A61B 17/663 606/57 |
| 6,302,687 B1 * | 10/2001 | King | A61B 17/663 433/18 |
| 6,322,566 B1 | 11/2001 | Minoretti et al. | |
| 6,423,069 B1 * | 7/2002 | Sellers | A61B 17/663 606/105 |
| 6,500,177 B1 * | 12/2002 | Martinelli | A61B 17/6458 606/54 |
| 6,786,890 B2 * | 9/2004 | Preuthun | A61M 5/14566 604/155 |
| 6,908,469 B2 | 6/2005 | Sellers et al. | |
| 7,875,033 B2 * | 1/2011 | Richter | A61B 17/66 606/280 |
| 7,981,118 B2 | 7/2011 | Mommaerts | |
| 2002/0018978 A1 | 2/2002 | Triaca et al. | |
| 2002/0035368 A1 * | 3/2002 | Schumacher | A61B 17/663 606/86 R |
| 2002/0040225 A1 * | 4/2002 | Sellers | A61B 17/663 606/105 |
| 2002/0116002 A1 * | 8/2002 | Sellers | A61B 17/663 606/71 |
| 2002/0156485 A1 * | 10/2002 | Sellers | A61B 17/663 606/105 |
| 2004/0000818 A1 * | 1/2004 | Preuthun | A61M 5/14566 310/83 |
| 2005/0234448 A1 * | 10/2005 | McCarthy | A61B 17/8004 606/57 |
| 2007/0162045 A1 | 7/2007 | Ahmad | |
| 2009/0118733 A1 * | 5/2009 | Orsak | A61B 17/60 606/60 |
| 2010/0104999 A1 * | 4/2010 | Bulloch | A61B 17/663 433/7 |
| 2012/0239035 A1 * | 9/2012 | Li | A61B 17/663 606/57 |
| 2012/0259332 A1 | 10/2012 | Bullogh et al. | |

* cited by examiner

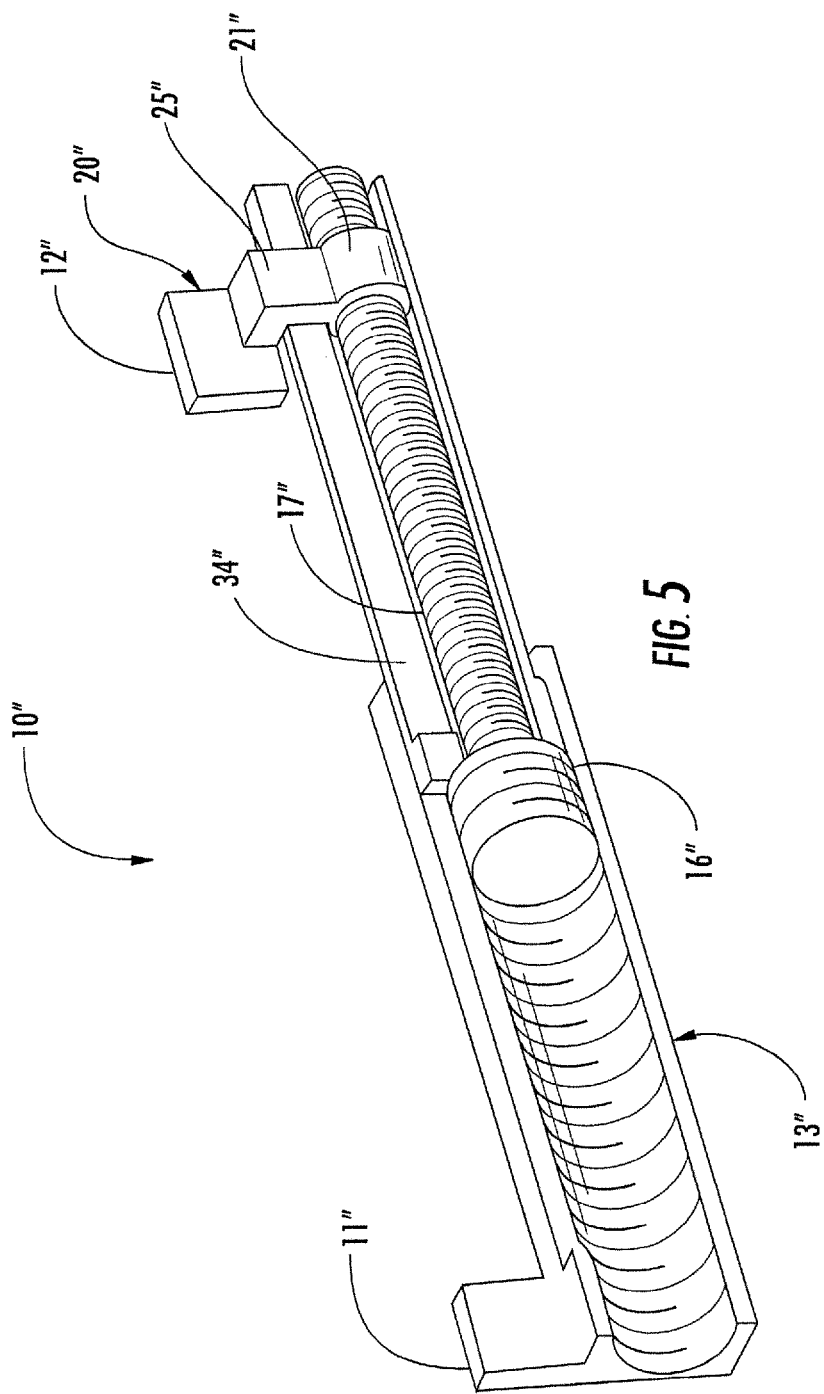

DISTRACTOR DEVICE INCLUDING MULTIPLE DIAMETER INTERNAL POST AND RELATED METHODS

FIELD OF THE INVENTION

The present invention relates to the field of medical devices, and, more particularly, to a distraction medical device and related methods.

BACKGROUND OF THE INVENTION

When a bone fracture occurs, normal bony healing occurs in a series of stages. Initially, there is the formation of a hematoma (blood clot) between the fractured bone ends and some inflammation associated with the fracture. In the next stage of the healing process, there is then recruitment of fibroblast cells for producing collagen within the fracture gap. The collagen matrix forms the scaffolding upon which new bone will be deposited. During this phase, there is also in-growth of new capillaries (neovascularization), thereby providing a blood supply to the area. The combination of the blood clot with fibroblasts and new blood vessels creates what is often referred to as a "soft callous" of bone within the fracture site.

In approximately 6-8 weeks, the soft callous begins to calcify and harden, and a "hard callous" is formed across the fracture site. Long-term, there is remodeling of the hard callous, i.e. the remodeling re-arranges the microscopic architecture of the new bone so that it becomes identical to the surrounding bone. This process can continue for as long as a year following the fracture.

Several approaches for selective reconstruction of bones using distraction have been disclosed. For example, U.S. Pat. No. 5,067,954 to Ilizarov discloses an medical device for distraction based plastic reconstruction of a hand. U.S. Pat. No. 4,978,347 to Ilizarov discloses a distraction device for short tubular bones.

For example, distraction procedures may be applied to correct skeletal growth discrepancies between the maxilla (upper jaw) and mandible (lower jaw), which can be the result of congenital defects, abnormal development/growth, trauma, or pathology. When a discrepancy in growth between the jaws occurs, the result may involve morphologic changes that affect the patient's facial appearance and functional disturbances, such as a nonfunctional occlusal (bite) relationship. Significant malocclusions may be associated with difficulty eating/chewing, and speaking. In cases where there is severe mandibular or maxillary deficiency, the patient's airway may be compromised resulting in obstructive sleep apnea or respiratory distress.

In general, patients with significant skeletal facial deformities cannot be treated with orthodontic treatment alone. In cases where the patient requires orthognathic (corrective jaw) surgery, osteotomies are created within one or both jaws, the position of the mandible and/or maxilla is corrected, and rigid fixation is applied. Surgical treatment is typically carried out when the patient has reached or is approaching skeletal maturity, which occurs following puberty.

Despite the high success rates of orthognathic surgical techniques, there are specific cases where typical procedures to advance the mandible and/or maxilla cannot be utilized. One application is where the desired advancement is beyond what can be achieved with a conventional osteotomy, i.e. an advancement of greater than 12 mm, and another application is mandibular advancement during the neonatal period because the size of the mandible in a newborn would not allow for conventional bone cuts and skeletal movements. In both applications, the approach involves the creation of osteotomies and the application of a device that would allow for gradual distraction (advancement/lengthening) of the bone segments, i.e. distraction osteogenesis.

Several devices for mandibular distraction osteogenesis have been disclosed. For example, U.S. Patent Application No. 2007/0162045 to Ahmad discloses a mandibular distractor device comprising a screw based track. U.S. Pat. No. 6,113,599 to Landsberger discloses a mandibular distractor device comprising a rotatable hub, and a pair of threaded arms extending therefrom. Yet another mandibular distraction device device is disclosed in U.S. Pat. No. 6,322,566 to Minoretti et al. and comprises a pair of extendable arms for implantation in the jaw bone of the patient.

Nevertheless, the typical mandibular distractor device may have drawbacks. For example, in mandibular distraction procedures for infant patients, the device may require a tracheotomy to permit access for adjustment subsequent to surgical implantation. Moreover, during the original implantation, the initial incision needed for typical mandibular distractor devices is significant, which may result in more scarring and trauma for the patient.

SUMMARY OF THE INVENTION

In view of the foregoing background, it is therefore an object of the present invention to provide a distractor device that is readily implanted into a patient.

This and other objects, features, and advantages in accordance with the present invention are provided by a distractor device that may comprise a tubular body being internally threaded, a first foot plate extending from the tubular body, and an internal post in the tubular body. The internal post may comprise a first portion having a first diameter being externally threaded to cooperate with the internally threaded tubular body, and a second portion coupled to the first portion, having a second diameter less than the first diameter, and also being externally threaded. The tubular body may comprise a longitudinal slot extending from adjacent the first foot plate. The distractor device may include a second foot plate extending through the longitudinal slot and for threadingly coupling to the externally threaded second portion of the internal post. The second portion may include a tool interface on a distal end thereof. Advantageously, the distractor device may be implanted with a reduced incision in a patient.

More specifically, the second foot plate may comprise a fixation portion, a medial connector portion extending from the fixation portion, and a ring portion coupled to the medial connector portion and being internally threaded for cooperating with the externally threaded second portion of the internal post. The fixation portion may define a plurality of openings for receiving fasteners, and the first foot plate may comprise a fixation portion defining a plurality of openings for receiving fasteners. For example, the first and second foot plates may be for fixation to at least one of a mandible bone and a long bone of a patient.

In some embodiments, the distractor device may further comprise a sheath surrounding the second portion. The longitudinal slot may extend from adjacent the first foot plate to a longitudinal end of the tubular body. The second portion may comprise a stop on the external threading thereof. Also, the tubular body may comprise a stop on the internal threading thereof. The distractor device may further comprise a motor coupled to the first portion.

Another aspect is directed to a distractor device that may comprise a tubular body being internally threaded, a first foot plate extending from the tubular body, and an internal post in the tubular body. The internal post may comprise a first portion having a first diameter being externally threaded to cooperate with the internally threaded tubular body, and a second portion coupled to the first portion, having a second diameter less than the first diameter, and also being externally threaded. The distractor device may also include a second foot plate for coupling to the internal post. The internal post may comprise a tool interface on a distal end thereof.

Another aspect is directed to a method of making a distractor device. The method may comprise forming a tubular body being internally threaded, and a first foot plate extending from the tubular body, and positioning an internal post in the tubular body. The internal post may comprise a first portion having a first diameter being externally threaded to cooperate with the internally threaded tubular body, and a second portion coupled to the first portion, having a second diameter less than the first diameter, and also being externally threaded, the tubular body comprising a longitudinal slot extending from adjacent the first foot plate. The method may include forming a second foot plate to extend through the longitudinal slot and for threadingly coupling to the externally threaded second portion of the internal post, the second portion comprising a tool interface on a distal end thereof.

Yet another aspect is directed to a method of making a distractor device. The method may comprise forming a tubular body being internally threaded, and a first foot plate extending from the tubular body, and positioning an internal post in the tubular body and comprising a first portion having a first diameter being externally threaded to cooperate with the internally threaded tubular body, and a second portion coupled to the first portion, having a second diameter less than the first diameter, and also being externally threaded. The method may also include forming a second foot plate for coupling to the internal post, the internal post comprising a tool interface on a distal end thereof.

BRIEF DESCRIPTION OF THE DRAWINGS

FIG. 5 is a perspective view of a CAD drawing of the distractor device of FIG. 4 in the activated position.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
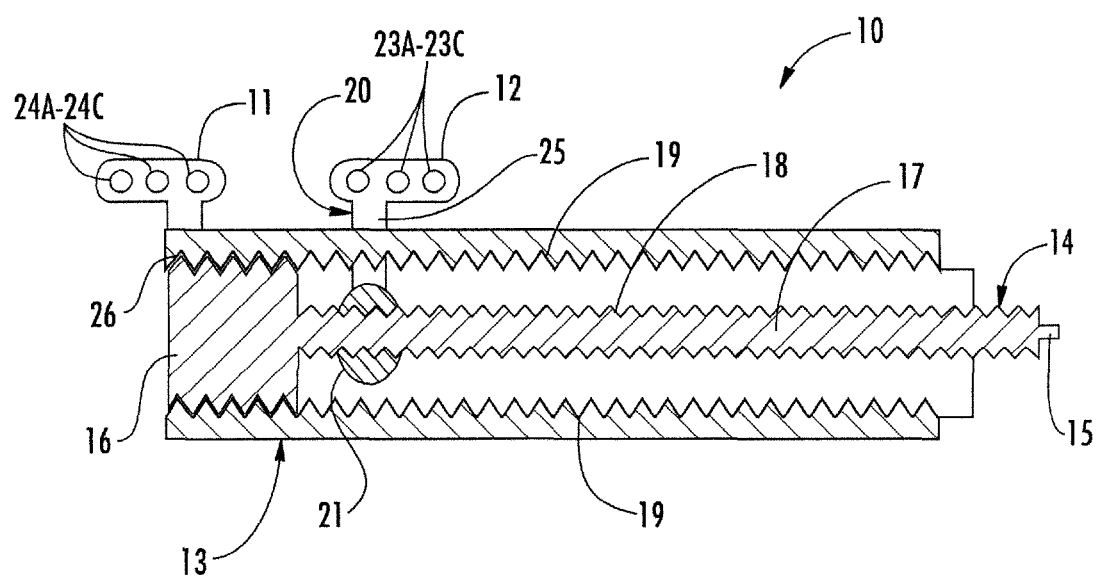
FIG. 1 is a cross-sectional view of the mandibular distractor device, according to the present invention.

Referring initially to FIG. 1, a mandibular distractor device 10 according to the present invention is now described. The mandibular distractor device 10 illustratively includes a tubular body portion 13 comprising internal threading 19, and a first foot plate 11 extending therefrom. The tubular body portion 13 is illustratively cylindrical in shape, but may be take other shapes, such as square, oval, or it may have a flattened-low-profile shape of some form.

The mandibular distractor 10 device illustratively includes an internal post 14 within the tubular body portion 13 and comprising a first cylindrical portion 16 having a first diameter and external threading 26 cooperating with the internal threading 19 of the tubular body portion, and a second cylindrical portion 17 coupled thereto. The second cylindrical portion 17 has a second diameter less than the first diameter and external threading 18. The tubular body portion 13 comprises a slot (not shown) extending from adjacent the first foot plate 11 to a longitudinal end of the tubular body portion. The mandibular distractor device 10 illustratively includes a second foot plate 20 extending through the slot in the tubular body portion 13 and for threadingly coupling to the second cylindrical portion 17 of the internal post 14. The internal post 14 may include a tool interface 15 for longitudinal advancement through the tubular body portion 13, and for also advancing the second foot plate 20 longitudinally along the internal post and the slot in the tubular body portion.

More specifically, the first foot plate 11 may illustratively define a plurality of openings 24a-24c for receiving fastening screws. The second foot plate 20 also illustratively defines a plurality of openings 23a-23c for receiving fastening screws, and includes a medial connector portion 25, and a ring portion 21 coupled to the medial connector portion and having internal threading for engaging the external threading 18 of the second cylindrical portion 17 of the internal post 14. For example, the first and second foot plates 11, 20 may comprise a bone plate, a bone clamp, a mesh plate, a hook, a bone screw or pin, or universal attachment for the purpose of attaching the mandibular distractor device 10 to bone.

As the internal post 14 is activated, the first cylindrical portion 16 travels along the length of the tubular body portion 13 and the second foot plate 20, in particular, the ring portion 21 thereof, travels along the threading 18 of the second cylindrical portion 17, thereby resulting in an "expanding" assembly. As will be appreciated by those skilled in the art, the number of turns in the threadings 18-19, 26 are selectively set to cause the second foot plate to travel to the end of the internal post 14 and to cause the first cylindrical portion 16 to correspondingly advance to an end of the tubular body portion 13 when the internal post has been fully activated, i.e. the mandibular distractor device 10 has been fully expanded. In some embodiments, the tubular body portion 13 includes an internal stop to prevent further activation of the internal post 14 once it has advanced fully. Moreover, the second cylindrical portion 17 may also include a stop on an end of the external threading 18 to prevent the second foot plate 20 from exceeding the length of the threading.

As will be appreciated by those skilled in the art, the mandibular distractor device 10 is illustratively shown for distraction procedures on the mandible. Nevertheless, the mandibular distractor device 10 can be used on other bone structures in the body, such as, for example, on the maxilla bone (upper jaw). Depending on the embodiment, modifications to the first and second foot plates 11, 20 may be necessary to provide proper fixation to the applicable bone. Nevertheless, the mandibular distractor device 10 may be further applied for distraction procedures on other facial bones, such as the orbits and the cranium, and other bones in the body, for example, the hand bones, the femur, the ribs, and the spine.

Advantageously, the mandibular distractor device 10 may be X mm in length at the time of initial implantation and have a capacity to "expand" in-situ to a length of 2X mm. For example, as a result of the mandibular distractor device 10, the surgeon may implant the mandibular distractor device with an initial size/length of 15 mm which allows for activation and lengthening of the bone to a total length of 30 mm. This allows the surgeon to make a smaller incision at the time of initial placement (as well as subsequent removal). By comparison, the typical devices include a "single-diameter" threaded post that is not capable of "expanding."

Figure 2:
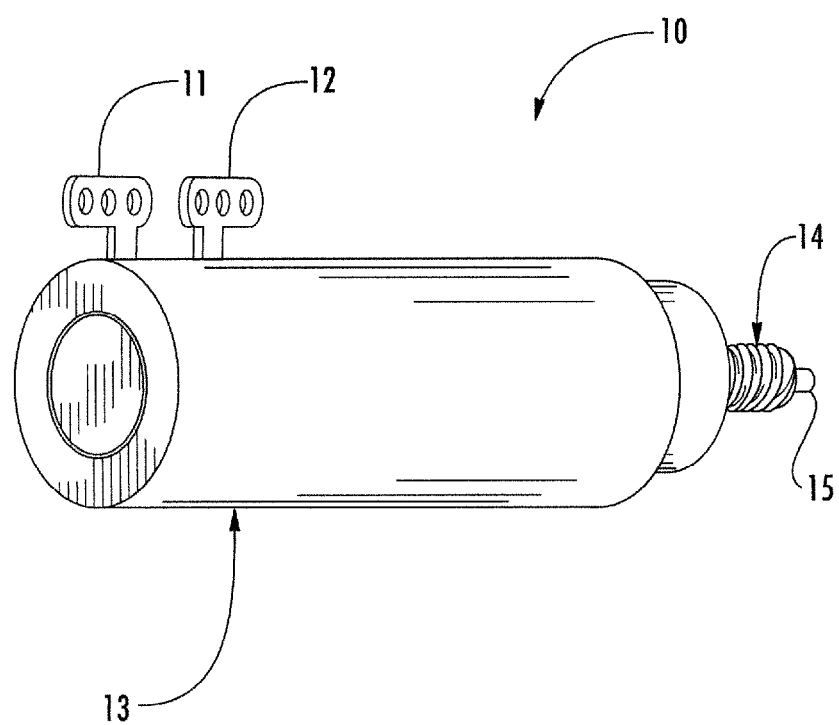
FIG. 2 is a side elevation view of the mandibular distractor device of FIG. 1.
Figure 3:
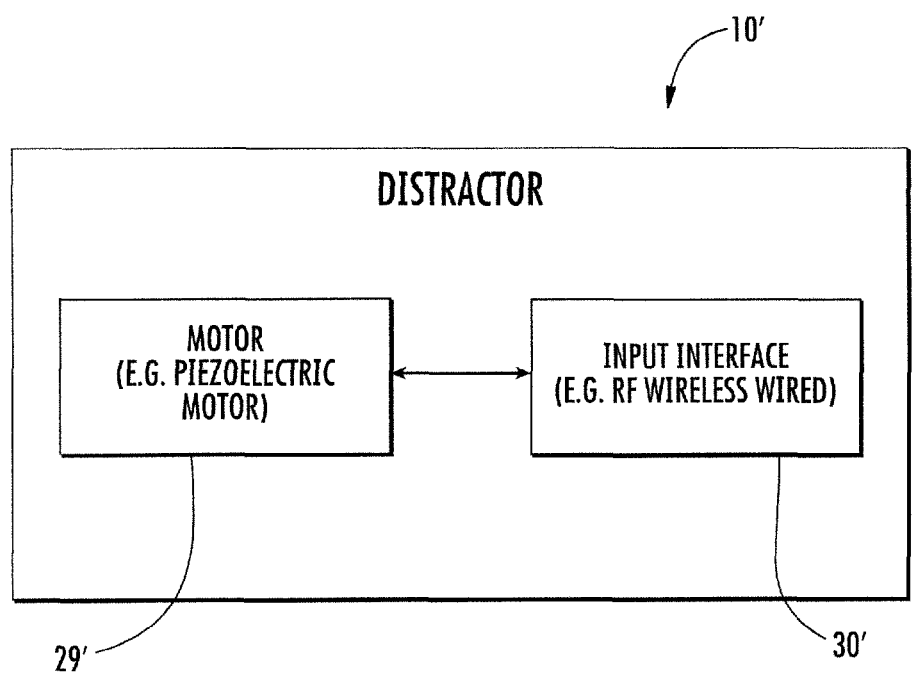
FIG. 3 is a schematic diagram of another embodiment of the distractor device of FIG. 1.

Referring now to FIG. 3, another embodiment of the distractor 10' is now described. In this embodiment of distractor 10', those elements already discussed above with respect to FIGS. 1-2 are given prime notation and most require no further discussion herein. This embodiment differs from the previous embodiment in that distractor 10' further includes a motor 29' for selectively rotating the internal post 14'. For example, the motor 29' may comprise a piezoelectric motor, such as the Squiggle motor, as available from New Scale Technologies, Inc. of Victor, N.Y. The "expanding" design of the mandibular distractor device 10' described herein may advantageously permit adding a motorized component. The result would be the mandibular distractor device 10' that is completely "internal" and does not require the surgeon or patient to turn the post or "jack-screw" because the motor does this as part of the assembly. For example, in the illustrated embodiment, the distractor 10' further includes an input interface 30' coupled to the motor 29', and for activating the motor. The input interface 30' may comprise one of an integrated controller, a control unit in cooperation with a percutaneous wire, or a wireless radio frequency (RF) controller (i.e. RF wireless receiver of some form).

Figure 4:
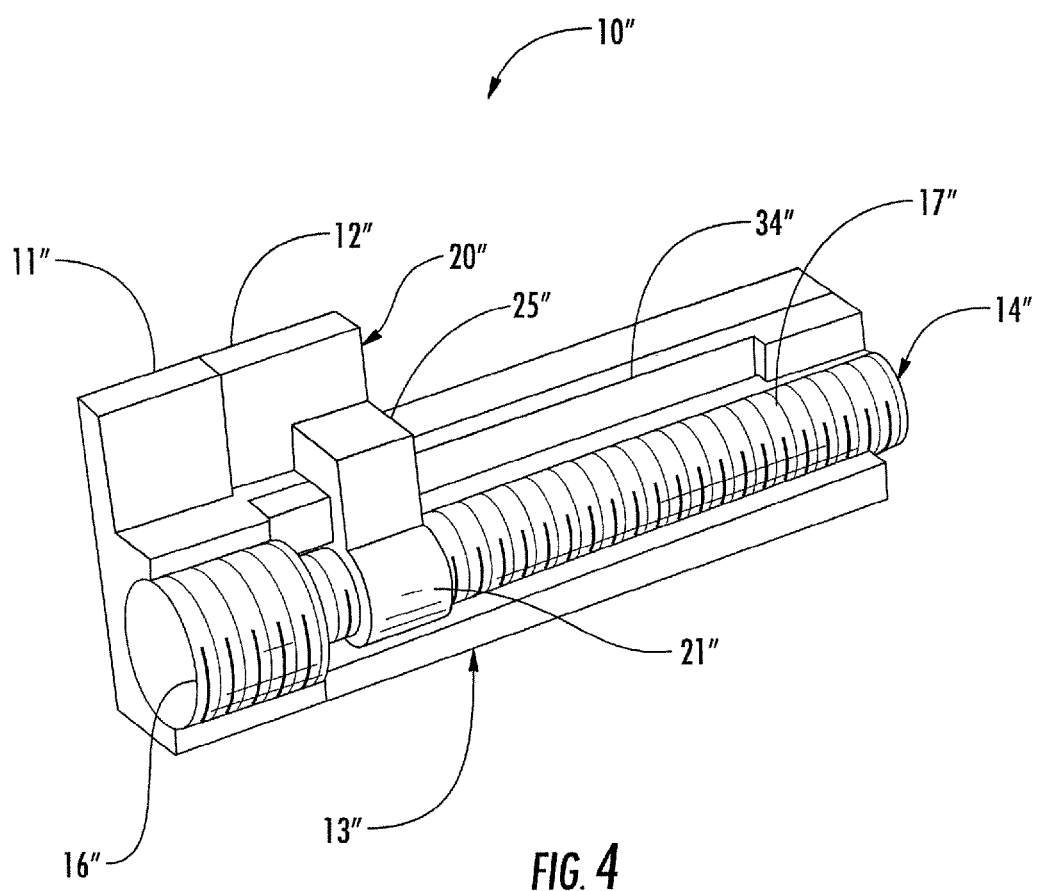
FIG. 4 is a perspective view of a CAD drawing of another embodiment of the distractor device of FIG. 1, with a portion of the tubular body portion removed.

Referring now to FIGS. 4-5, another embodiment of the distractor 10" is now described. In this embodiment of distractor 10", those elements already discussed above with respect to FIGS. 1-2 are given double prime notation and most require no further discussion herein. This embodiment differs from the previous embodiment in that distractor 10" further includes a sheath 34" for covering the second cylindrical portion 17" as it is activated and longitudinally extends from the tubular body portion 13".

Another aspect is directed to a method of making a distractor device 10. The method may comprise forming a tubular body 13 being internally threaded, and a first foot plate 11 extending from the tubular body, and positioning an internal post 14 in the tubular body. The internal post 14 may comprise a first portion 16 having a first diameter being externally threaded to cooperate with the internally threaded tubular body 13, and a second portion 17 coupled to the first portion, having a second diameter less than the first diameter, and also being externally threaded, the tubular body comprising a longitudinal slot extending from adjacent the first foot plate. The method may include forming a second foot plate 20 to extend through the longitudinal slot and for threadingly coupling to the externally threaded second portion of the internal post 14, the second portion 17 comprising a tool interface 15 on a distal end thereof.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the disclosure.

That which is claimed is:

1. A distractor device comprising:
   a tubular body being internally threaded;
   a first foot plate extending from said tubular body;
   an internal post in said tubular body and comprising a first portion having a first diameter being externally threaded to cooperate with said internally threaded tubular body and defining a proximal end, and a second portion being in immovably fixed relation to said first portion and defining a distal end, having a second diameter less than the first diameter, and also being externally threaded; and
   a second foot plate for coupling to said internal post;
   said internal post comprising a tool interface on a distal most end thereof, the tool interface actuating extension of said second foot plate from a first position retracted adjacent the first foot plate to a second position extended opposite to the first foot plate, and actuating extension of said internal post within said tubular body.

2. The distractor device of claim 1 wherein said first and second foot plates are for fixation to at least one of a mandible bone, a maxilla bone, and a long bone of a patient.

3. The distractor device of claim 1 further comprising a sheath surrounding said second portion.

4. The distractor device of claim 1 wherein said second portion comprises a stop on the external threading thereof.

5. The distractor device of claim 1 wherein said tubular body comprises a stop on the internal threading thereof.

6. The distractor device of claim 1 further comprising a motor coupled to said first portion.

7. A distractor device comprising:
   a tubular body being internally threaded;
   a first foot plate extending from said tubular body;
   an internal post in said tubular body and comprising a first portion having a first diameter being externally threaded to cooperate with said internally threaded tubular body and defining a proximal end, and a second portion being in immovably fixed relation to said first portion and defining a distal end, having a second diameter less than the first diameter, and also being externally threaded; and
   a second foot plate longitudinally traveling along with said internal post;
   said internal post comprising a tool interface on a distal most end thereof, the tool interface actuating extension of said second foot plate from a first position retracted adjacent the first foot plate to a second position extended opposite to the first foot plate, and actuating extension of said internal post within said tubular body.

8. The distractor device of claim 7 wherein said first and second foot plates are for fixation to at least one of a mandible bone, a maxilla bone, and a long bone of a patient.

9. The distractor device of claim 7 further comprising a sheath surrounding said second portion.

10. The distractor device of claim 7 wherein said second portion comprises a stop on the external threading thereof.

11. The distractor device of claim 7 wherein said tubular body comprises a stop on the internal threading thereof.

12. The distractor device of claim 7 further comprising a motor coupled to said first portion.

13. A method for making a distractor device comprising:
    forming a tubular body being internally threaded, and a first foot plate extending from the tubular body;
    positioning an internal post in the tubular body and comprising a first portion having a first diameter being externally threaded to cooperate with the internally threaded tubular body and defining a proximal end, and a second portion being in immovably fixed relation to the first portion and defining a distal end, having a second diameter less than the first diameter, and also being externally threaded; and
    positioning a second foot plate for coupling to the internal post;
    the internal post comprising a tool interface on a distal most end thereof, the tool interface actuating extension of the second foot plate from a first position retracted adjacent the first foot plate to a second position extended opposite to the first foot plate, and actuating extension of the internal post within the tubular body.

14. The method of claim 13 wherein the first and second foot plates are for fixation to at least one of a mandible bone, a maxilla bone, and a long bone of a patient.

15. The method of claim 13 further comprising positioning a sheath surrounding the second portion.

16. The method of claim 13 wherein the second portion comprises a stop on the external threading thereof.

17. The method of claim 13 wherein the tubular body comprises a stop on the internal threading thereof.

18. A method for making a distractor device comprising:
    forming a tubular body being internally threaded, and a first foot plate extending from the tubular body;
    positioning an internal post in the tubular body and comprising a first portion having a first diameter being externally threaded to cooperate with the internally threaded tubular body and defining a proximal end, and a second portion being in immovably fixed relation to the first portion and defining a distal end, having a second diameter less than the first diameter, and also being externally threaded; and
    positioning a second foot plate longitudinally traveling along with the internal post;
    the internal post comprising a tool interface on a distal most end thereof, the tool interface actuating extension of the second foot plate from a first position retracted adjacent the first foot plate to a second position extended opposite to the first foot plate, and actuating extension of the internal post within the tubular body.

19. The method of claim 18 wherein the first and second foot plates are for fixation to at least one of a mandible bone, a maxilla bone, and a long bone of a patient.

20. The method of claim 18 further comprising positioning a sheath surrounding the second portion.

21. The method of claim 18 wherein the second portion comprises a stop on the external threading thereof.

* * * * *